(12) United States Patent
Videen

(10) Patent No.: US 7,440,102 B1
(45) Date of Patent: Oct. 21, 2008

(54) SYSTEMS AND METHODS FOR ANALYZING POLARIZED LIGHT SCATTERED FROM A SAMPLE

(75) Inventor: Gorden Videen, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 2 days.

(21) Appl. No.: 11/211,560

(22) Filed: Aug. 26, 2005

(51) Int. Cl.
  *G01N 21/00* (2006.01)
(52) U.S. Cl. ...................................... 356/342
(58) Field of Classification Search ........................ None
  See application file for complete search history.

(56) References Cited

U.S. PATENT DOCUMENTS

| | | | |
|---|---|---|---|
| 4,154,529 A | 5/1979 | Dyott | |
| 4,492,467 A | 1/1985 | Drain et al. | |
| 5,063,301 A | 11/1991 | Turkevich et al. | |
| 5,294,806 A | 3/1994 | Batchelder et al. | |
| 5,561,515 A | 10/1996 | Hairston et al. | |
| 5,627,642 A | 5/1997 | Dhadwal et al. | |
| 5,999,257 A | 12/1999 | Myers et al. | |
| 6,034,776 A | 3/2000 | Germer et al. | |
| 6,042,998 A | 3/2000 | Brueck et al. | |
| 6,138,083 A | 10/2000 | Videen | |
| 6,239,873 B1 | 5/2001 | Videen | |
| 6,411,441 B1 | 6/2002 | Videen | |
| 6,414,797 B1 | 7/2002 | Videen | |
| 6,587,200 B1 | 7/2003 | Riebel et al. | |
| 6,674,528 B2 | 1/2004 | Adachi et al. | |
| 6,704,105 B1 | 3/2004 | Swanson et al. | |
| 6,744,507 B2 | 6/2004 | Yamaguchi | |
| 6,774,994 B1 | 8/2004 | Wyatt et al. | |
| 2006/0197952 A1* | 9/2006 | Chen et al. | 356/445 |

OTHER PUBLICATIONS

H. H. Qui and W. Jia ; Effect Of Refractive Index In Optical Particle Using Spatial Frequency Method ; pp. 190-210 ; Optical Communications 178 ; 2000.

(Continued)

*Primary Examiner*—Tarifur Chowdhury
*Assistant Examiner*—Michael LaPage
(74) *Attorney, Agent, or Firm*—William R. Randolph; Christos S. Kyriakou

(57) ABSTRACT

Systems for analyzing polarized light back-scattered from a sample are provided. An exemplary system comprises an optical beamsplitter, a polarization separator and an array of light detectors. The optical beamsplitter is operative to receive an incident ray of light, to direct at least a portion of the incident ray to a sample, to receive a back-scattered ray from the sample, and to reflect at least a portion of the back-scattered ray as a reflected back-scattered ray. The polarization separator is located to receive the reflected back-scattered ray and is operative to divide the reflected back-scattered ray into a transverse-electric (TE) component and a transverse-magnetic (TM) component. The array of light detectors is located to receive the TE component and the TM component and is operative to acquire information corresponding to the respective intensities of the TE component and the TM component simultaneously. Methods and other systems also are provided.

18 Claims, 4 Drawing Sheets

OTHER PUBLICATIONS

Michael Mischenko; On The Nature Of The Polarization Opposition Effect Exhibited By Saturn's Rings; pp. 351-361; The Astrophysical Journal 411; 1993.

Gordon Videen ; Polarization Opposition Effect And Second-Order Ray Tracing; pp. 5115-5121; Applied Optics vol. 41; Issue 24; Aug. 2002.

Karri Muinonen; Coherent Backscattering Of Light By Complex Random Media Of Spherical Scatterers: Numerical Solution pp. 365-388, Institute Of Physics PublishingWaves Random Media 14; 2004.

Yu. Shkuratov et. al.; Opposition Effect From Clementine Data And Mechanisms Of Backscatter; pp. 132-155; Icarus 141; 1999.

Vera Rosenbush et. al.; Polarization Properties Of The Galilean Satellites Of Jupiter Observations And Preliminary Analysis; 402-414; The Astrophysical Journal 487; Sep. 20, 1997.

Karri Muinonen; Coherent Backscattering By Solar System Dust Particles; pp. 271-296; Asteroids, Comets and Meteors; 1993.

Yu. Shkuratov; The Opposition Effect And Negative Polarization Of Structural Analogs For Planetary Regoliths; pp. 396-416; Icarus 159; 2002.

M. I. Mishchenko; Enhanced BackscatteringOf Polarized Light From Discrete Random Media; Calculations In Exactly The Backscattering Direction; pp. 978-982; Journal Optical Society of America vol. 9, No. 6; 1992.

M. I. Mishchenko; Polarization Effects In Weak Localization Of Light: Calculation Of The Copolarized And Depolarized Backscattering Enhancement Factors 4 pages The American Physical Society vol. 44-22 1991.

Michael Mischchenko; Full Angular Profile Of The Coherent Polarization Opposition Effect; pp. 888-891; Journal Optical Society of America vol. 17 No. 5 May 2000.

Ismo Lindell, et al: Scattering By A Small Object Close To An Interface. I. Exact-Image Theory Formulation; pp. 472-476 Journal Optical Society Of America vol. 8 No. 3 Mar. 1991.

K. Muinonen; Scattering By A Small Object Close To An Interface. II. Study Of Backscattering; pp. 477-482; Journal Optical Society Of America vol. 8 No. 3 Mar. 1991.

Karri Muinonen; Coherent Backscattering By Absorbing And Scattering Media; pp. 223-226; Sixth Conference On Light Scattering By Nonspherical Particles.

J.E. Geake and M. Geake; A Remote-Sensing Method For Sub-Wavelength Grains On Planetary Surfaces By Optical Polarimetry pp. 46-55 Mon Not B astr Soc 245 1990.

Milo Wolff; Polarization Of Light Reflected From Rough Planetery Surface; pp. 1395-1405; Applied Optics, vol. 14 No. 6 Jun. 1975.

Karri Muinonen; Scattering Of Light By Solar System Dust: The Coherent Backscatter Phenomenon; pp. 12-15 Proceedings Of The Finnish Astronomical Society Helsinki 1990.

Nadia Zakharova, et. al.; Scattering Properties Of Needlelike And Platelike Ice Spheriods With Moderate Size Parameters 5052-5057 Applied Optics vol. 39 No. 27 Sep. 20, 2000.

* cited by examiner

POLARIZATION STATE vs. θ

SYSTEMS AND METHODS FOR ANALYZING POLARIZED LIGHT SCATTERED FROM A SAMPLE

GOVERNMENT INTEREST

The invention described herein may be manufactured, used, and licensed by or for the United States Government.

BACKGROUND

1. Technical Field

The present disclosure relates to optics. Specifically, the disclosure relates to systems and methods that involve the use of polarized light that is scattered from samples.

2. Description of the Related Art

Measurements of back-scattered light are of interest for several reasons. By way of example, remote sensing techniques, such as light detection and ranging (LIDAR), analyze back-scattered light. Back-scattered light also can provide information about the size distribution of particles of a scattering system. Specifically, photons traveling reversed paths constructively interfere in the back-scatter region. This leads to a peak in the exact back-scatter direction that is inversely proportional to the length of the path difference. Hence, the back-scattered light provides a measure of the spatial properties of the scattering system.

Spatial properties are used to define and describe parameters of a system. For example, a set of spatial properties for a system may include elements relating to location, change in location, speed, trajectory (straight or curved), orientation, relation of parts to the whole system, and spatial relations among adjacent objects. Examples of shape properties may include form of the shape, size, number of parts, form of the parts, and symmetry or asymmetry, and examples of surface properties could include color(hue), saturation or intensity, texture and temporal patterns (blinking or pulsating). Spatial frequency and amplitude are other spatial properties often used to define a system. An analogous example of a distribution of spatial frequencies are waves coming onto a shore. The waves can be really close together (having high spatial frequencies) or further apart (having lower spatial frequencies). Another property is the amplitude of these spatial frequencies, such as the height of the waves. Further, spatial properties such as spatial frequencies and amplitudes, the mean spatial frequency and its standard deviation, and the root mean square (rms) roughness of the system can be used to characterize properties such as a surface, particles in a cloud, or an aggregate of spores. Thus, the root mean square (rms) amplitude of the surface roughness of both waves may be the same, but the conditions of the waves are different. Specifically, the spatial frequencies of the cloud of particles may relate to the density of the cloud, where the larger the density of the cloud, the higher the spatial frequencies of the cloud particles. A further example is an aggregate of spores where the spatial frequency of the aggregate is dependent upon the size of the particles making up the aggregate. Example of the use of spatial frequencies use in analyzing systems are disclosed in U.S. Pat. Nos. 6,034,776 (Germer et al) and 6,042,998 (Brueck et al) and "Effect Of Refractive Index In Optical Particle Using Spatial Frequency Method", H. H. Qui, W. Jia, Optical Communication 178 (2000) 199-210, all of which are fully incorporated herein.

In analyzing particle systems with light or optical means, measurement of light back-scattered from particles and surfaces can be difficult. For instance, some devices for measuring back-scatter require two measurements to be taken at different times. This is problematic when the scattering system is time dependent, such as when particles are passed through a flow cytometer.

Methods and apparatus for measuring or determining characteristics of particles, such as size and velocity, with optical means are disclosed in U.S. Pat. Nos. 4,154,529 (Dyott); 4,492,467 (Drain et. al.); 5,063,301 (Turkevich et. al.); 5,294,806 (Batchelder et. al.); 5,561,515 (Hairston et. al.); 5,627,642 ((Dhadwal et. al.); 5,999,257 (Myers et. al.); 6,587,200 (Riebel et. al.); 6,674,528 (Adachi et. al.); 6,704,105 (Swanson et. al.); 6,744,507 (Yamaguchi); 6,774,994 (Wyatt et. al.); and 6,778,271 (Watson et. al.), all of which are fully incorporated herein.

SUMMARY

Systems and methods for analyzing polarized light back-scattered from a sample are provided. In this regard, an embodiment of a system comprises an optical beamsplitter, a polarization separator and an array of light detectors. The optical beamsplitter is operative to receive an incident ray of light, to direct at least a portion of the incident ray to a sample, to receive a back-scattered ray from the sample, and to reflect at least a portion of the back-scattered ray as a reflected back-scattered ray. The polarization separator is located to receive the reflected back-scattered ray and is operative to divide the reflected back-scattered ray into a transverse-electric (TE) component and a transverse-magnetic (TM) component. An array of light detectors is located to receive the TE component and the TM component and is operative to acquire information corresponding to the respective intensities of the TE component and the TM component simultaneously.

One embodiment for analyzing polarized light back-scattered from a sample comprises the steps of: receiving back-scattered light from a sample; separating the back-scattered light into a transverse-electric (TE) component and a transverse-magnetic (TM) component; and directing the TE component and the TM component to an array of light detectors such that the array acquires information corresponding to the respective intensities of the TE component and the TM component simultaneously.

Another embodiment comprises the steps of: providing an incident ray of light; propagating the incident ray through an optical beamsplitter such that at least a portion of the incident ray is directed to a sample; illuminating the sample with the portion of the incident ray that was directed to the sample; receiving, at the optical beamsplitter, a back-scattered ray from the sample; redirecting at least a portion of the back-scattered ray with the optical beamsplitter to form a reflected back-scattered ray; separating the reflected back-scattered ray into a transverse-electric (TE) component and a transverse-magnetic (TM) component; and acquiring information corresponding to the respective intensities of the TE component and the TM component. A database of known spatial properties and/or particle characteristics, such as threat particles, is acquired by measuring the position and depth of a minimum under various conditions, especially the number of particles in the cluster. This acquiring a database of test data for various types of particles and conditions would be a calibration step. When the device is used in the field, the actual acquired test data is measured and compared with the database containing a library of known and calibrated test results.

Other devices, systems, methods, features and/or advantages will be or may become apparent to one with skill in the art upon examination of the following drawings and detailed description. It is intended that all such additional devices, systems, methods, features and/or advantages be included within this description.

BRIEF DESCRIPTION OF THE DRAWINGS

Many aspects of the disclosure can be better understood with reference to the following drawings. Note, the components in the drawings are not necessarily to scale. Also, like reference numerals designate corresponding parts throughout the several views.

DETAILED DESCRIPTION

As will be described in detail here, systems and methods are provided that can be used for analyzing polarized light scattered from a sample, such as a particle system. An exemplary embodiment of such a system includes an optical beamsplitter that is used to direct light to a sample. The sample scatters the light, a portion of which is back-scattered. The optical beamsplitter receives light back-scattered from the sample and reflects a portion of the back-scattered light. The back-scattered light is divided into a transverse-electric (TE) polarization component and a transverse-magnetic (TM) polarization component. The TE and TM components are directed to an array of light detectors, which acquire information corresponding to the respective intensities of the TE and TM components. Measurements of the TE and TM components then can be used to determine information, such as polarization state as a function of back-scattering angle ($\theta$) for the sample, for example. This information can be used to estimate characteristics of the sample, e.g., particle size and distance between particles.

Figure 1:
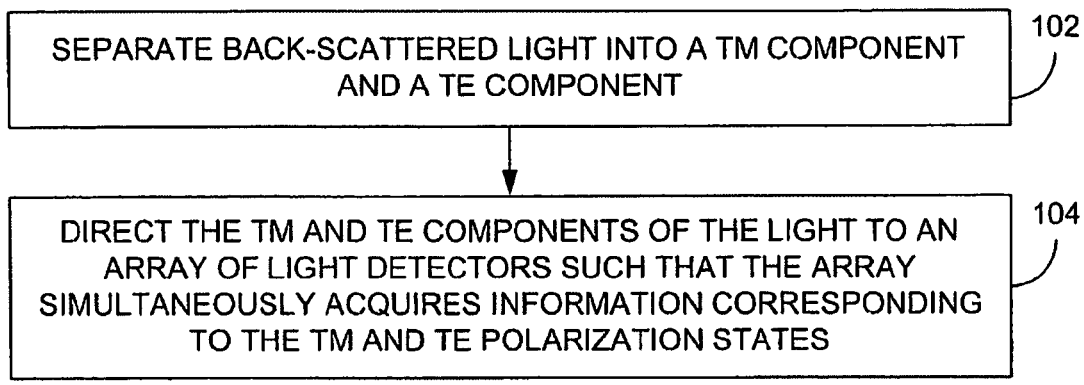
FIG. 1 is a flowchart of an embodiment of a method for analyzing polarized light back-scattered from a sample.

An embodiment of a method for analyzing polarized light scattered from a sample is depicted in the flowchart of FIG. 1. As shown in FIG. 1, the method may be construed as beginning at block 102, where light that has been back-scattered from a sample is separated into a TM polarization component and a TE polarization component. In block 104, the TM and TE polarization components of the light are directed to an array of light detectors so that the array simultaneously acquires information corresponding to the TM and TE polarization states. As should be understood, this can alleviate the need for taking measurements at different times. Thus, such a method may be particularly suited for analyzing time-dependent scattering systems.

Figure 2:
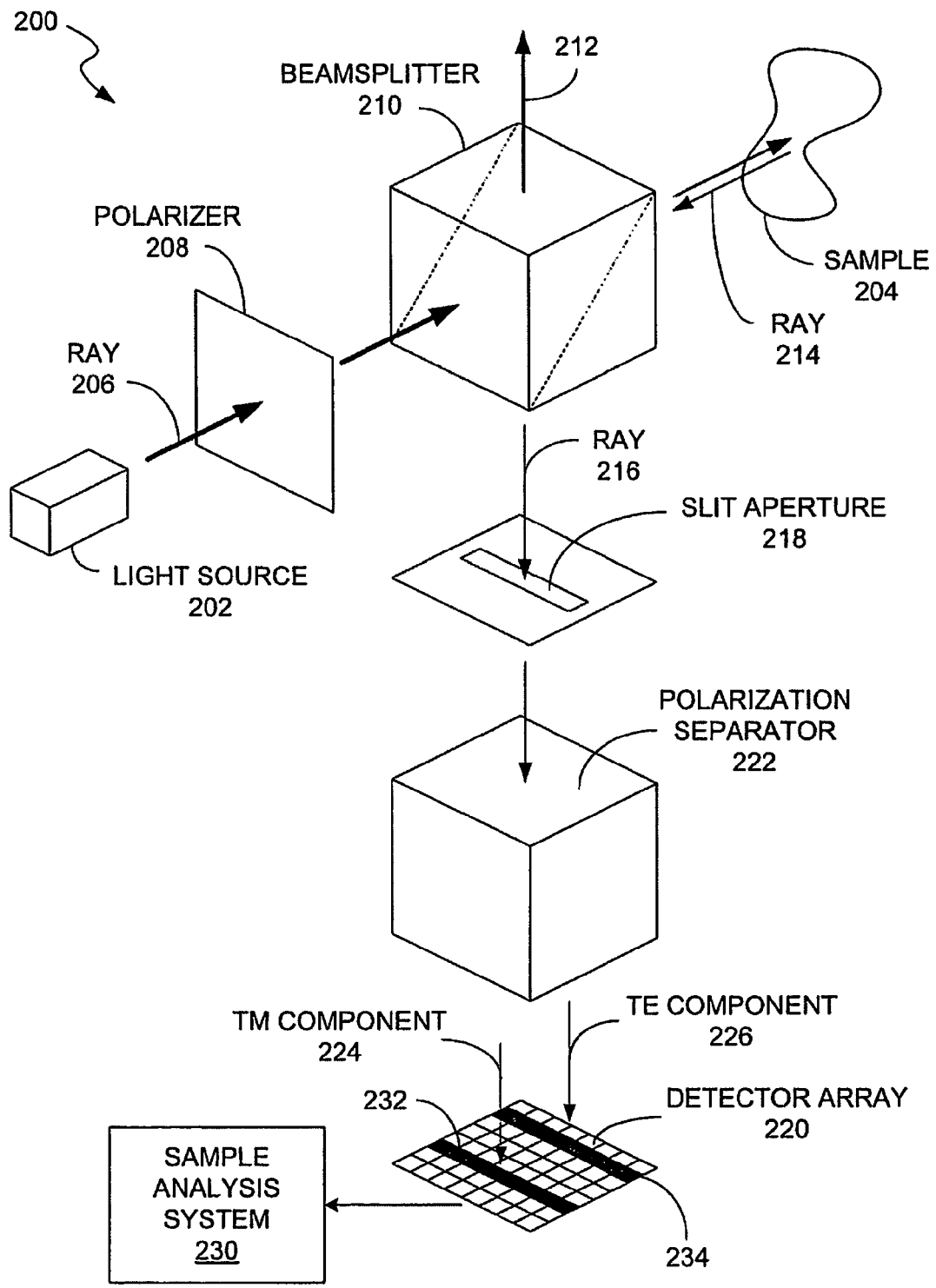
FIG. 2 is a schematic diagram of an embodiment of a system for analyzing polarized light back-scattered from a sample.

An embodiment of a system that can be used for performing the method of FIG. 1 is depicted schematically in FIG. 2.

As shown in FIG. 2, system 200 includes a light source 202, such as a laser, that is used to provide light for illuminating a sample 204. Light source 202 provides an incident ray 206 to a polarizer 208. By way of example, polarizer 208 can be a circular polarizer that filters the incident ray so that the light arriving at the sample 204 is initially illuminated by an equal amount of each polarization component. Alternatively, the polarizer 208 could be a linear polarizer oriented at 45 degrees to the scattering plane.

From the polarizer 208, the incident ray propagates to an optical beamsplitter 210, depicted as a cubic shaped beamsplitter, although other shapes are permissible. The beamsplitter 210 divides the incident ray so that a portion of the incident ray illuminates sample 204. The other portion of the incident ray is propagated from the beamsplitter as a reflected ray 212, which typically is not used in analysis of the sample.

Sample 204 scatters the incident ray. Note, only back-scattered ray 214 is depicted as being scattered by the sample in FIG. 2. As shown in FIG. 2, the back-scatter angle ($\theta$) is the value of the angle formed between the incident ray and the back-scattered ray. The back-scattered ray 214 is propagated to beamsplitter 210, which reflects a portion of the back-scattered ray as reflected back-scattered ray 216. Reflected back-scattered ray 216 is directed to a slit aperture 218, which spatially modifies, i.e., alters the cross section of, the reflected back-scattered ray 216 so that the light will be aligned with light detectors 232 and 234 of detector array 220. Specifically, the slit aperture 218 forms a beam of the back-scattered light. The cross section of this beam has a large aspect ratio, with locations along the major axis of the beam corresponding to a range of scattering angles from the back-scattered direction.

Prior to being incident upon the array 220, the reflected back-scattered ray 216 is provided to the polarization separator 222. In FIG. 2, the polarization separator is a block of birefringement material, such as calcite. The birefringement material divides the reflected back-scattered ray into two components; a component 224 corresponding to the TM polarization state, and a component 226 corresponding to the TE polarization state. The birefringement material causes components 224 and 226 to be laterally displaced from each other. TE component 224 is the TE-polarization component of the scattered light as a function of scattering angle along its length. Similarly, TM component 226 is the TM-polarization component of the scattered light as a function of scattering angle along its length. Note that the minor axis of the beam provided by the slit aperture is shorter than the separation distance between the TE and TM components achieved by a polarization separator 222.

Components 224 and 226 are directed to the light detectors 232 and 234 of detector array 220. In response to the TM and TE components being incident thereupon, the light detectors 232 and 234 of the array 220 acquire information corresponding to the TM and TE polarization states. Specifically, the light detectors, e.g., photodiodes, accumulate charge corresponding to an intensity of light being incident thereupon and a duration of exposure. The information then can be provided to sample analysis system 230 for analysis. By way of example, the sample analysis system 230 can correlate the acquired information at each detector pixel element with the scatter angles at which the information was acquired, and can perform various calculations for determining characteristics of the sample 204. The sample analysis system 230 includes a database of previously recorded test ample analysis information including tests of similar systems of particles under varying combinations of spatial properties such as spacing, size, velocity, density, etc. This could be considered a calibration step. Then, the real time test data would be compared with pre-recorded database information to determine the particular spatial properties of the system. A particularly useful application would be the detection of threat particles by comparing the detected results with the position and depth of the minimum (i.e. POE depicted in FIG. 7) under various conditions, such as the number of agglomerates in detected clusters.

Because the back-scattered light was divided into two components, two portions of the array of light detectors are illuminated. Since the back-scattered light was shaped by passage through a slit aperture, these portions appear as illuminated bands 232 and 234 on the detector array 220. Based upon the type of materials and particular geometry used, the relative positions of the TE and TM components are fixed. Thus, information acquired by the array can be attributed to the appropriate polarization state (TE or TM) of the light. Information acquired can be used to determine various relationships, such as intensity of TE versus back-scatter angle ($\theta$), intensity of TM versus back-scatter angle ($\theta$), and percent polarization versus back-scatter angle.

Note, in some embodiments, at least a portion of the system 200, e.g., beamsplitter 210, can be rotated relative to the sample so that information can be acquired over a larger range of field angles.

Figure 3:
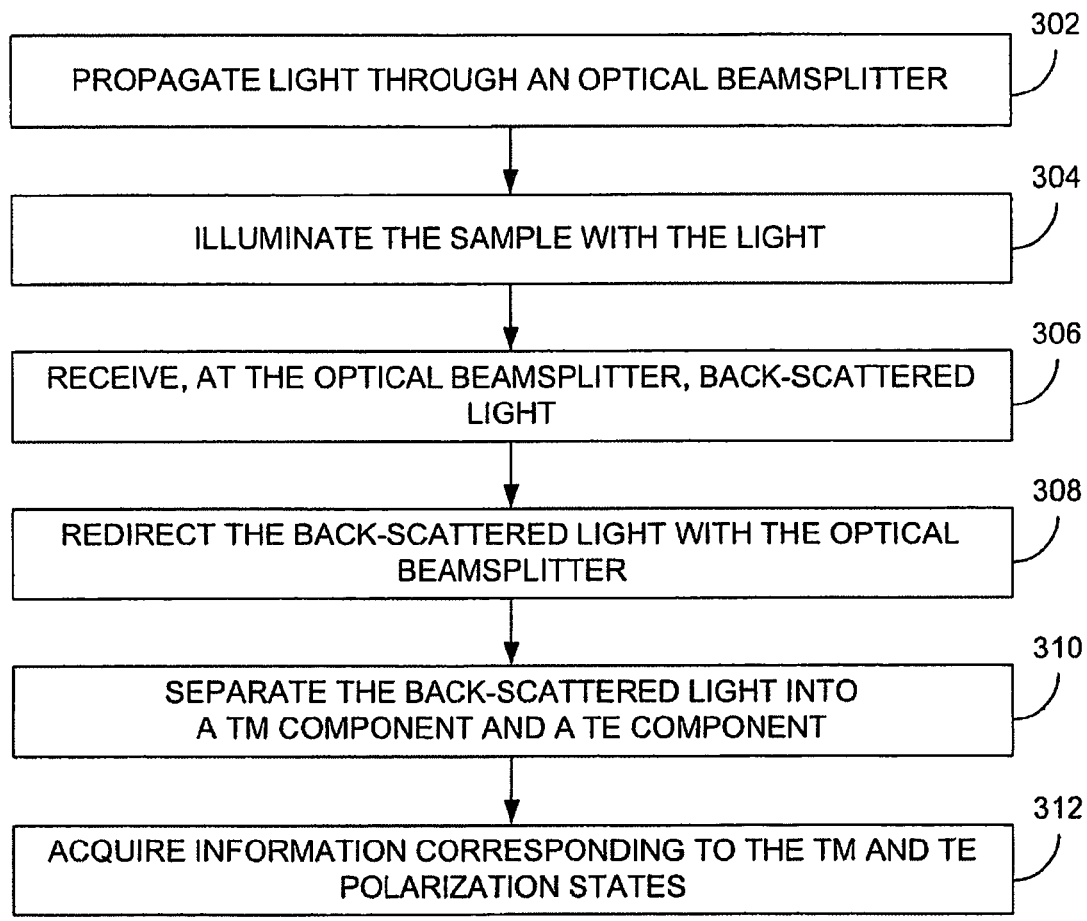
FIG. 3 is a flowchart depicting functionality of the embodiment of FIG. 2.

Reference will now be made to the flowchart of FIG. 3, which depicts functionality of an embodiment of a system for analyzing polarized light scattered from a sample. As depicted in FIG. 3, the method may be construed as beginning at block 302, where an incident ray of light is propagated through an optical beamsplitter so that at least a portion of the incident ray is directed to a sample. In block 304, the sample is illuminated with a portion of the incident ray. In block 306, a back-scattered ray from the sample is received at the optical beamsplitter. In block 308, at least a portion of the back-scattered ray is redirected with the optical beamsplitter to form a reflected back-scattered ray. In block 310, the reflected back-scattered ray is separated into a TE component and a TM component. Then, as depicted in block 312, information corresponding to the respective intensities of the TE component and the TM component is acquired.

Information corresponding to the TE and TM components can be used in various manners. By way of example, the information can be stored in a memory, such as in a database, and/or can be provided in graphical form. FIGS. 4-7 graphically depict representative information corresponding to the TE and TM components of back-scattered light acquired from a sample.

Figure 4:
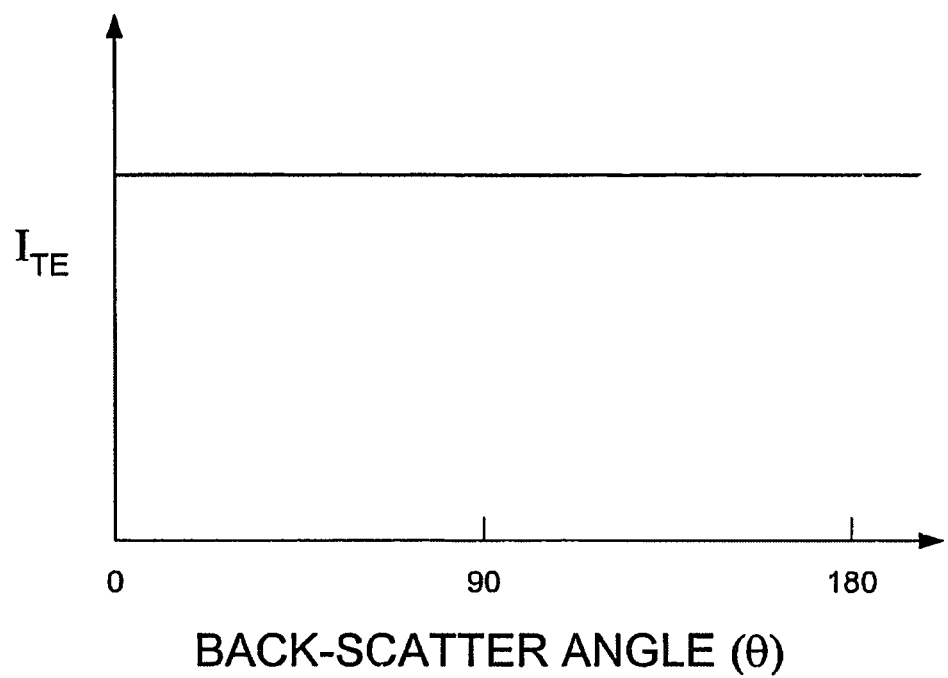
FIG. 4 is a graph depicting intensity of TE polarization state versus back-scatter angle ($\theta$) for a single small spherical particle.
Figure 5:
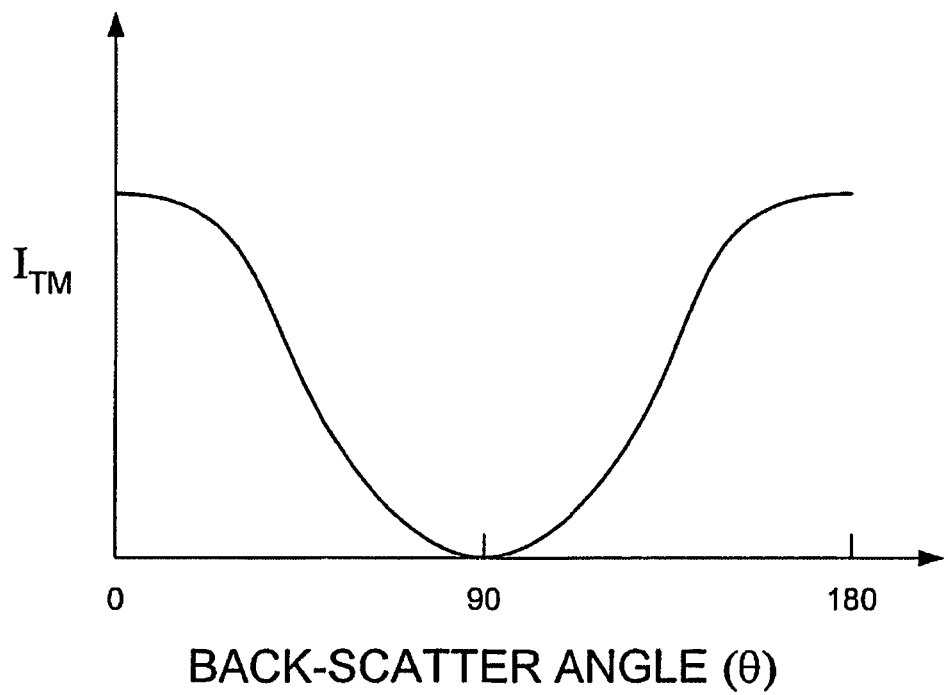
FIG. 5 is a graph depicting intensity of the TM polarization state versus back-scatter angle ($\theta$) for a single small spherical particle.
Figure 6:
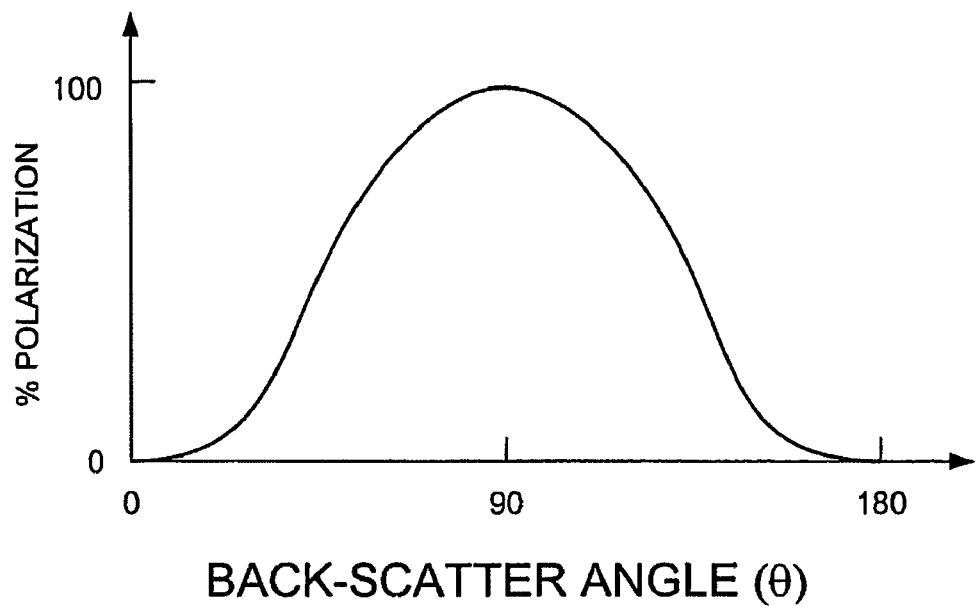
FIG. 6 is a graph depicting percent polarization versus back-scatter angle ($\theta$) for a single, small spherical particle, as determined by $(I_{TE} - I_{TM})/(I_{TE} + I_{TM})$.

As shown in FIG. 4, the intensity of the TE component ($I_{TE}$) for a single, small spherical particle is plotted against the back-scatter angles ($\theta$) at which the information was acquired. Similarly, as shown in FIG. 5, the intensity of the TM component ($I_{TM}$) for that particle is plotted versus the back-scatter angle ($\theta$). Using the information presented in FIGS. 4 and 5, percent polarization for the particles is plotted versus back-scatter angle ($\theta$) as shown in FIG. 6, as determined by $(I_{TE}-I_{TM})/(I_{TE}+I_{TM})$. Note that back-scatter angle ($\theta$)=180°− (i.e., minus) the forward scatter angle. Due to symmetry of small particle systems, however, the graphs of FIGS. 4-6 appear the same whether plotted against the forward or the back-scatter angle ($\theta$).

Figure 7:
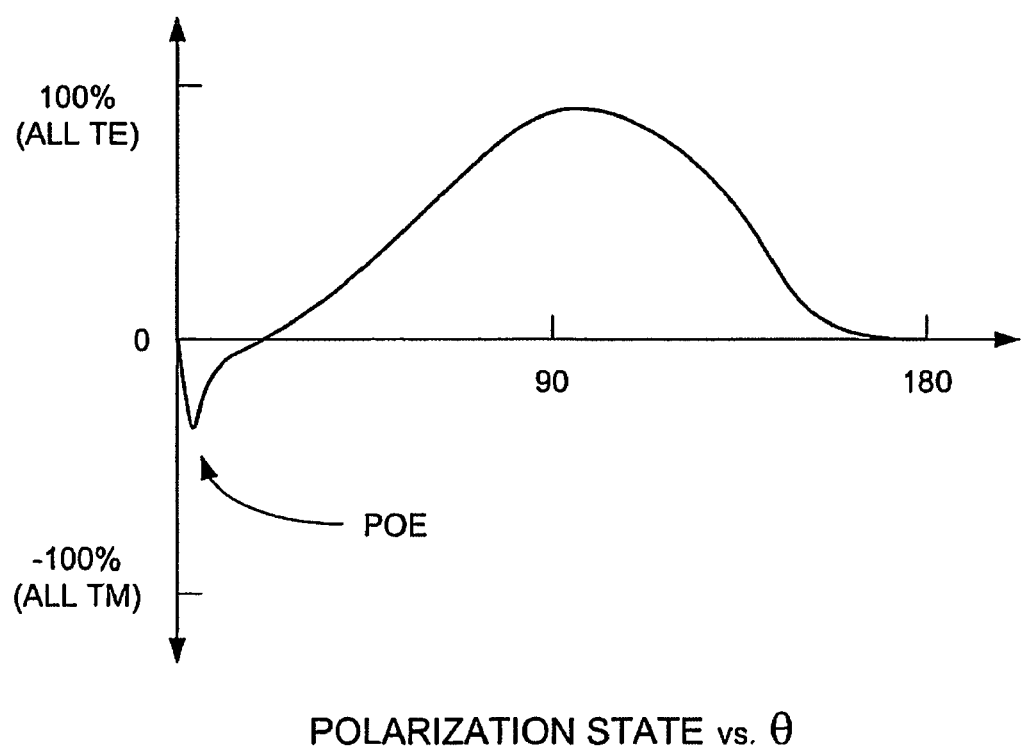
FIG. 7 is a graph depicting polarization state versus back-scatter angle ($\theta$) for a cloud of small interacting spherical particles, as determined by $(I_{TE} - I_{TM})/(I_{TE} + I_{TM})$.

FIG. 7 depicts percent polarization versus back-scatter angle for a representative sample of interest, in this case, a cloud of small interacting spherical particles, as determined by $(I_{TE}-I_{TM})/(I_{TE}+I_{TM})$. Note that the polarization opposition effect (POE) is evident in FIG. 7. The POE refers to the negative polarization exhibited in the near back-scatter region, i.e., at back-scatter angles ($\theta$)<10°–20°. Discussions about backscattering and/or POE include the following articles/documents:

U.S. patent application Ser. No. 10/642,676 filed Aug. 19, 2003 by Gordon Videen, entitled Systems And Methods For Analyzing Particle Systems Using Polarized Scattered Light;

U.S. patent application Ser. No. 10/642,677 filed Aug. 19, 2003 by Gordon Videen, entitled Systems And Methods For Analyzing Particle Systems Of Surface Facets Using Polarized Scattered Light;

Michael Mishchenko, "On The Nature Of The Polarization Opposition Effect Exhibited By Saturn's Rings", pages 351-361, The Astrophysical Journal 411, 1993;

Gordon Videen, "Polarization Opposition Effect And Second-Order Ray Tracing", pages 5115-5121, Applied Optics, Volume 41, Issue 24, August 2002;

Karri Muinonen, "Coherent Backscattering Of Light By Complex Random Media Of Spherical Scatterers Numerical Solution", pages 365-388, Institute Of Physics, Publishing Waves Random Media 14, 2004;

Yu. Shkuratov et. al.; Opposition Effect From Clementine Data And Mechanisms Of Backscatter; pages 132-155; Icarus 141; 1999;

Vera Rosenbush et. al.; Polarization Properties Of The Galilean Satellites Of Jupiter Observations And Preliminary Analysis; 402-414; The Astrophysical Journal 487; Sep. 20, 1997;

Karri Muinonen; Coherent Backscattering By Solar System Dust Particles; pages 271-296; Asteroids, Comets and Meteors; 1993;

Yu. Shkuratov; The Opposition Effect And Negative Polarization Of Structural Analogs For Planetary Regoliths; pages 396-416; Icarus 159; 2002;

M. I. Mishchenko; Enhanced Backscattering Of Polarized Light From Discrete Random Media; Calculations In Exactly The Backscattering Direction; pages 978-982; Journal Optical Society of America Vol. 9, No 6; 1992;

M. I. Mishchenko; Polarization Effects In Weak Localization Of Light: Calculation Of The Copolarized And Depolarized Backscattering Enhancement Factors; 4 pages; The American Physical Society, Vol. 44-22; 1991;

Michael Mishchenko; Full Angular Profile Of The Coherent Polarization Opposition Effect; pages 888-891; Journal Optical Society of America, Vol. 17, No. 5; May 2000;

Ismo Lindell, et al; Scattering By A Small Object Close To An Interface. I. Exact-Image Theory Formulation; pages 472-476; Journal Optical Society of America, Vol. 8, No. 3; March 1991;

Karri Muinonen; Coherent Backscattering By Absorbing And Scattering Media; pages 223-226; Sixth Conference On Light Scattering By Nonspherical Particles;

J. E. Geake and M. Geake; A Remote-Sensing Method For Sub-Wavelength Grains On Planetary Surfaces By Optical Polarimetry; pages 46-55; Mon. Not. R. astr Soc. 245; 1990;

Milo Wolff; Polarization Of Light Reflected From Rough Planetary Surface; pages 1395-1405; Applied Optics, Vol. 14, No. 6; June 1975;

Karri Muinonen; Scattering Of Light By Solar System Dust: The Coherent Backscatter Phenomenon; pages 12-15; Proceedings Of The Finnish Astronomical Society, Helsinki; 1990; and Nadia Zakharova, et. al.; Scattering Properties Of Needlelike And Platelike Ice Spheroids With Moderate Size Parameters; 5052-5057; Applied Optics, Vol. 39, No. 27; Sep. 20, 2000.

The teachings of all of the above are fully incorporated herein by reference. Thus, the POE can be analyzed to determine various characteristics of the sample of interest, such as spatial frequency of the sample. Specifically, the angular position of the POE minima is inversely proportional to the spatial frequency.

In FIG. 7 a dip in the graph is shown occurring between about 0 to 15 degrees. The dip in FIG. 7 graph provides information about the particle system, such as the spatial frequencies. When the dip is located closer to zero, this indicates the presence of longer path lengths, which correspond to lower spatial frequencies, which would correspond to a cluster of larger particles, whereas, if the dip is farther from zero, the particles in the cluster would be smaller. To a first-order approximation, the characteristic size (and hence, path length) is the size of the spore. This spore size determines the position of the minimum. So, this minimum position is going to be located at a different position than that produced by a cluster of other spores, or by a dust particle, or by other things. Most importantly, it doesn't matter so much how many particles form the cluster, the minimum position (to first-order approximation) will remain at approximately the same location. So a cluster of 5 spores or 50 spores will have the same warning signal, because the spores are self-similar, the signal is especially strong and can be distinguished from that of a randomly shaped dust particle of similar size. That is, the minimum is especially deep for a cluster of similar particles, like anthrax spores.

It should be emphasized that many variations and modifications may be made to the above-described embodiments. By way of example, modifications can be made to the ordering of some of the components/functions depicted in the embodiments presented in this disclosure. For instance, light sources can be used that provide unpolarized light. Additionally or alternatively, various types of optical beamsplitters other than the cubic beamsplitter depicted in FIG. 2 can be used in some embodiments. By way of example, spherically-shaped and cylindrically-shaped beamsplitters can be used. Beamsplitters are described in greater detail in U.S. Pat. No. 6,414,797, entitled "Beamsplitter Prism with Spherical Faces for Transmitting or Reflecting Spherical Waves Without Magnification," U.S. Pat. No. 6,411,441, entitled "Beamsplitter Prism with Cylindrical Faces for Transmitting or Reflecting Cylindrical Waves Without Magnification, the teachings of which are fully incorporated herein. All such modifications and variations are intended to be included herein within the scope of this disclosure and protected by the following claims.

What is claimed is:

1. A system for analyzing polarized light back-scattered from a sample, the system comprising:

an optical beamsplitter means operative to receive an incident ray of light, to direct at least a portion of the incident ray to a sample, to receive a back-scattered ray from the sample, and to reflect at least a portion of the back-scattered ray as a reflected back-scattered ray;

a polarization separator located to receive the reflected back-scattered ray, the polarization separator being operative to divide the reflected back-scattered ray into a transverse-electric (TE) component and a transverse-magnetic (TM) component;

an array of light detectors located to receive the TE component and the TM component, the array being operative to acquire information corresponding to the respective intensities of the TE component and the TM component; and a slit aperture located to receive the reflected back-scattered ray from the optical beamsplitter means, the slit aperture being operative to modify the reflected back-scattered ray spatially prior to the polarization separator receiving the modified reflected back-scattered ray.

2. The system of claim 1, wherein:

the light detectors of the array are arranged in rows and columns; and the slit aperture is oriented such that a major axis of the slit aperture is parallel to either the columns or the rows of the light detectors.

3. The system of claim 1, further comprising:

a sample analysis system operative to receive the information corresponding to the respective intensities of the TE component and the TM component, to analyze the information, and to estimate a characteristic of the sample using the information.

4. A system for analyzing polarized light back-scattered from a cloud of particles for an incident ray of light and for different back-scattering angles (Θ), where a back-scatter angle (Θ) is the angle between an incident ray of light striking the cloud of particles and the reflected light back-scattered from the cloud of particles, the system comprising:

an optical beamsplitter for receiving an incident ray of light, for directing at least a portion of the incident ray to the cloud of particles separated and spaced from the beamsplitter, for receiving back-scattered rays from the cloud of particles, and for reflecting at least a portion of the back-scattered ray as a reflected back-scattered ray;

a polarization separator located to receive the reflected back-scattered ray, the polarization separator dividing the reflected back-scattered rays into transverse-electric (TE) and transverse-magnetic (TM) components; and an array of light detectors located to receive the TE and TM components, the array being operative to acquire simultaneous information corresponding to the respective intensities of the TE component and the TM component.

5. The system of claim 4, further comprising:

a sample analysis system operative to receive the information corresponding to the respective intensities of the TE component and the TM component at different back-scatter angles (Θ), to analyze the information, and to estimate a characteristic of the cloud of particles using the information.

6. The system of claim 4, further comprising:

a polarizer located to receive the incident ray of light, the polarizer being operative to impart a selected polarization to the incident ray and then provide the incident ray to the optical beamsplitter.

7. The system of claim 6, wherein the polarizer comprises a circular polarizer.

8. The system of claim 4, wherein the polarization separator comprises birefringment material for separating the TE component and the TM component.

9. The system of claim 4, wherein the polarization separator comprises calcite.

10. The system of claim 4, further comprising:

A slit aperture located to receive the reflected back-scattered ray from the optical beamsplitter means, the slit aperture being operative to modify the reflected back-scattered ray spatially prior to the polarization separator receiving the modified reflected back-scattered ray.

11. The system of claim 4, wherein:

the light detectors of the array are arranged in rows and columns.

12. A system for analyzing polarized light back-scattered from a sample of particles at different orientations of incident rays of light and backscatter angles (Θ) to estimate a characteristic of the sample of particles, and where a spatial frequency of the sample of particles is correlated with the angular position of the polarization opposition effect (POE), and where a backscatter angle ($\Theta$) is the angle between incident rays of light striking the sample of particles and the reflected light rays back-scattered from the sample of particles, the system comprising:
an optical beamsplitter means for receiving incident rays of light, for directing at least a portion of the incident rays to the sample of particles, for receiving back-scattered rays from the sample of particles, and for reflecting at least a portion of the back-scattered rays as reflected back-scattered rays;
a polarization separator located to receive the reflected back-scattered rays, the polarization separator dividing the reflected back-scattered rays into a transverse-electric (TE) component and transverse-magnetic (TM) component;
an array of light detectors located to receive the TE and the TM components, the array being operative to acquire simultaneous information corresponding to the respective intensities of the TE and TM component; and
means for comparing the TE and TM component information to estimate the polarization opposition effect (POE) and spatial properties for the sample of particles.

13. A method for analyzing polarized light back-scattered from a sample, where a back-scatter angle ($\Theta$) is the angle between an incident ray of light striking the sample and a back-scattered ray reflected from the sample, the method comprising the steps of:
providing an incident ray of light;
propagating the incident ray through an optical beamsplitter such that at least a portion of the incident ray is directed to a sample;
illuminating the sample with the portion of the incident ray that was directed to the sample;
receiving a back-scattered ray from the sample;
redirecting at least a portion of the back-scattered ray to form a reflected back-scattered ray;
spatially modifying the reflected back-scattered ray;
separating the back-scattered ray into a transverse-electric (TE) component and a transverse-magnetic (TM) component; and
acquiring information corresponding to the respective intensities of the TE component and the TM component at different back-scatter angles ($\Theta$) and determining a spatial property of the sample therefrom.

14. A method for analyzing polarized light back-scattered from a sample of particles, where a back-scatter angle ($\Theta$) is the angle between an incident ray of light striking the sample of particles and a back-scattered ray reflected from the sample of particles, the method comprising the steps of:
providing an incident ray of light;
propagating the incident ray through an optical beamsplitter such that at least a portion of the incident ray is directed to a sample;
illuminating the sample with the portion of the incident ray that was directed to the sample;
receiving a back-scattered ray from the sample;
redirecting at least a portion of the back-scattered ray to form a reflected back-scattered ray;
separating the back-scattered ray into a transverse-electric (TE) component and a transverse-magnetic (TM) component; and
acquiring information corresponding to the respective intensities of the TE component and the TM component at different back-scatter angles ($\Theta$), estimating a polarization opposition effect (POE) minima; and
determining a spatial frequency of the sample from the minima.

15. A method for analyzing polarized light back-scattered from a sample of particles at different backscatter angles ($\Theta$) to estimate a characteristic of the sample of particles and where a spatial frequency of the sample of particles is correlated with the angular position of the polarization opposition effect (POE), and where a backscatter angle ($\Theta$) is the angle between an incident light ray striking the sample of particles and a back-scattered light ray reflected from the sample of particles, the method comprising:
providing an incident ray of light;
propagating the incident ray through an optical beamsplitter such that at least a portion of the incident ray is directed to a sample;
illuminating the sample with the portion of the incident ray that was directed to the sample;
receiving a back-scattered ray from the sample;
redirecting at least a portion of the back-scattered ray with the optical beamsplitter to form a reflected back-scattered ray;
separating the back-scattered ray into a transverse-electric (TE) component and a transverse-magnetic (TM) component; and
acquiring information corresponding to the respective intensities of the TE component and the TM component and determining a spatial property of the sample therefrom.

16. The method of claim 15, further comprising:
spatially modifying the back-scattered ray prior to separating the back-scattered ray into the TE component and the TM component.

17. The method of claim 15, including:
acquiring information comprising angular position of a polarization opposition effect (POE) minima; and
estimating a spatial frequency of the sample therefrom.

18. The method of claim 15, wherein:
the information comprises an angular position of a polarization opposition effect (POE) minima.

* * * * *